United States Patent [19]

Vandevelde et al.

[11] 4,451,446

[45] May 29, 1984

[54] PROCESS FOR THE PREPARATION OF POLYSACCHARIDE-PROTEIN COMPLEXES FROM BACTERIAL CAPSULES, OBTAINED PRODUCTS AND IMMUNOGENIC COMPOSITIONS CONTAINING THEM

[75] Inventors: Jean Vandevelde, Ottignies-Louvain-la-Neuve; Robert De Neys, Rixensart, both of Belgium

[73] Assignee: Smithkline-Rit, Belgium

[21] Appl. No.: 354,878

[22] Filed: Mar. 4, 1982

[51] Int. Cl.$^3$ .................. A61K 39/102; A61K 37/00; C07G 7/00

[52] U.S. Cl. ........................... 424/92; 424/88; 424/180; 424/177; 536/1.1; 260/112 R

[58] Field of Search ............... 424/92, 88, 177, 180; 260/112 R; 536/1

[56] References Cited

U.S. PATENT DOCUMENTS

| | | | |
|---|---|---|---|
| 3,636,192 | 1/1972 | Gotschlich | 424/92 |
| 4,220,717 | 9/1980 | Kuo | 424/92 |
| 4,264,764 | 4/1981 | Kniskern et al. | 424/92 |

OTHER PUBLICATIONS

Anderson et al., J. Infect. Dis., 136, S63–S70, (1977).
Anderson et al., J. Infect. Dis., 144, 509–520, (1981).
Anderson et al., J. Infect., Dis., 144, 530–538, (1981).
Zollinger et al., J. Infect. Dis., 137, 728–739, (1978).
Zollinger et al., J. Clin. Invest., 63, 836–848, (1979).
Schneerson et al., J. Expt. Med., 152, 361–376, (1980).
Anderson et al., NTIS Report PB 80-171036, (May 30, 1979).
Anderson et al., NTIS Report PB 297238, (Apr. 15, 1977).
Anderson et al., Pediat. Res. 14, 771, (1980).
Anderson et al., 14th Intersc. Conf. Antim. Ag. Chemother. Abstract 157, (1974).
Anderson et al., J. Infect. Dis., 136, 557–562, (1977).
Rodgrigues et al., J. Immunol, 107, 1071–1080, (1971).
Chemical Abstracts, vol. 90, Abstract No. 4291b, 1979.
Anderson et al., J. Clin. Invest., 51, 31–38, (1972).
Laemmli Nature, 227, 680–685, (1970).
Anderson et al., Infect. and Immun., 13, 581–589, (1976).
Moore et al., J.A.M.A., 199, 519–524, (1967).

Primary Examiner—Blondel Hazel
Attorney, Agent, or Firm—Edward T. Lentz; Janice E. Williams; Alan D. Lourie

[57] ABSTRACT

Process for the non-degrading preparation of polysaccharide-protein complexes from bacterial capsules; the so-obtained products which are useful as vaccines against infection by the same bacteria and method for protecting human beings against the same infection by administration of pharmaceutical composition containing the polysaccharide-protein complexes.

13 Claims, No Drawings

PROCESS FOR THE PREPARATION OF POLYSACCHARIDE-PROTEIN COMPLEXES FROM BACTERIAL CAPSULES, OBTAINED PRODUCTS AND IMMUNOGENIC COMPOSITIONS CONTAINING THEM

The present invention relates to a process for the preparation of polysacharide-protein complexes from bacterial capsules, to the obtained products and to the immunogenic preparations containing them.

The virulence of certain bacteria is due to the possible presence of a capsule which envelopes the outer membrane and which is made up of different components, among which polysaccharides and proteins.

Examples of such capsulated bacteria are *Neisseria meningitidis, Neisseria gonorrhea, Haemophilus influenzae* and *Escherichia coli.*

The process of this invention and the herein obtained products are not related to the use of a particular strain within a species since the only requirement for the starting microorganism in the process is to be a capsulated bacterium of the considered species, i.e. a well known starting material which can be easily obtained from clinical infection cases and typified by those skilled in the art.

For instance, the Neisseriae are well known microorganisms which can be easily isolated from typical clinical infection cases. They are non-motile, Gram negative small cocci (about 0.6 $\mu$m $\times$ 1.0 $\mu$m) which grow simply but often in pairs with adjacent sides flattened or occasionally in tetrads or clusters.

The Neisseriae are essentially aerobic but also multiply under microaerophilic conditions. Among them, *Neisseria meningitidis* group B is responsible for an important proportion of meningococcal diseases in some countries.

In J. Clin. Invest. 63: 836–848: 1979, W. D. Zollinger et al. report that after having combined partially purified polysaccharide of *Neisseria meningitidis* group B from one culture with outer membrane proteins prepared from a second culture grown under the same conditions and processed the mixture further to remove lipopolysaccharides, the final preparation was immunogenic in man.

*Haemophilus influenzae* also is a well-known Gram negative pathogen that occurs in both non-capsulated and capsulated forms. Capsulated *Haemophilus influenzae* contains capsular polysaccharides of one of 6 types (a to f), among which type b is a pathogen of paticularly serious consequence, especially for young children: *Haemophilus influenzae* type b (Hi.b) is indeed one of the most common bacteria responsible for bacterial meningitis in children less than 6 years of age.

Organisms seen in pathologic samples such as cerebrospinal fluid are generally small and capsulated Gram negative non-motile coccobacillary to rod-shaped cells (0.2 $\mu$m–0.3 $\mu$m $\times$ 0.5 $\mu$m–2.0 $\mu$m). Non capsulated strains are markedly pleomorphic and filamentous.

On solid medium capsulated virulent strains appear as small "dewdrop" colonies and, on transparent medium, such as Levinthal agar, these are characteristically iridescent in obliquely transmitted light. After 24–48 hrs. the capsules and iridescence disappear, and autolysis and a variable Gram stain reaction occur. Both the autolysis and capsular destruction are apparently caused by activation of endogenous enzymes. Similarly, in liquid medium the capsules disappear early in cultures.

*Haemophilus influenzae* is a facultative anaerobe which requires two growth factors present in blood; the heat-stable X and the labile V.

The six types, designated types a to f, have been described; these are serologically identified by agglutination, precipitation or quellung tests performed with specific antisera.

In type b, the most important pathogen type for humans, the capsular polysaccharide contains ribose, ribitol and phosphate and this polyribosylribitol phosphate is herein designated PRR'P.

A process for the culture of *Haemophilus influenzae type b and the isolation of polyribosylribitol phosphate the capsular polysaccharide of Haemophilus influenzae* type b is described by L. P. Rodrigues et al. in J. Immunol. 107: 1071–1080, 1971 and a process for the isolation and purification of polyribosylribitol phosphate from *Haemophilus influenzae type b is given in U.S. Pat. No. 4,220,717.*

Strains of *Haemophilus influenzae* type b have been deposited with the American Type Culture Collection (ATCC), Rockville, Md., USA where they were given accession numbers ATCC 9745 and ATCC 10211 respectively and these strains are obtainable therefrom. Alternatively and as indicated above, strains of *Haemophilus influenzae* type b can also be easily isolated from typical infection cases. Any of these strains and any of the processes for the culture of the microorganism as described in the hereinabove indicated reference can be used in the process for preparing the immunogenic polyribosylribitol phosphate-protein complexes of the present invention.

Development of an *Haemophilus influenzae* type b vaccine for very young children—i.e. under two years of age—is still in the early stages. A purified polysaccharide vaccine gave encouraging preliminary results but was later shown to induce only a very poor immune response in children under two years of age (P. Anderson et al. J. Inf. Dis. 136: S 57–62, 1977). The immunogenicity of a polyribosylribitol phosphate-protein complex from *Haemophilus influenzae* type b was also studied in weanling rabbits by P. Anderson and D. H. Smith (J. Inf. Dis. 136: S 63–70, 1977): in this study the authors indicate that in an effort to analyse the fact that PRR'P is more effectively immunogenic when it is associated with the bacterium than when it is in the purified form, they isolated from *Haemophilus influenzae* type b a high molecular weight soluble complex in which PRR'P appears to be combined with proteins, the pyrogenicity and limulus lysate gelation activity of the complex suggesting the presence of a small amount of lipolysaccharides.

We have found that the immunogenicity of the isolated polysaccharide-protein complex is not dependent on the presence of lipopolysaccharides which are pyrogenic and thus undesirable ingredients but on the amount and nature of the protein present therein. We have also found that the noncovalent bound between the polysaccharide and the protein is particularly labile in liquid medium in the presence of products such as cetrimonium bromide and ethanol which are usually employed in the preparation of capsular bacterial polysaccharide complexes.

According to the invention there is provided a process for preparing immunogenic lipopolysaccharide-free bacterial capsular polysaccharide-protein noncovalent complexes from bacteria suspended in an aqueous medium which is for instance a whole broth culture medium of a wild pathogenic isolate of a bacterium in capsulated form, which process comprises the inactivation of the bacteria by the addition of a quaternary ammonium salt (e.g. cetrimonium bromide) immediately followed by the collection of the insoluble fraction, take up with a 0.2 to 2 N aqueous solution of a non-toxic alkali or alkaline-earth metal salt such as sodium chloride, calcium chloride or magnesium chloride and preferably calcium chloride, precipitation of contaminants (mainly nucleic acids) by addition of from 5 to 40% (vol/vol) of a water-miscible alcohol (preferably 25% of ethanol), removal of the quaternary ammonium salt from the solution by formation of a water insoluble salt thereof, e.g. by addition of a water soluble iodide, sulfocyanide or benzoate which is preferably an alkaline metal salt and separation of the precipitate to yield an aqueous solution from which said complex is isolated, for instance by concentrating the solution by ultrafiltration and lyophilisation.

As it will appear from the examplification, the amount of protein in the complex may vary according to the particular operative conditions, e.g. the concentration and/or nature of the employed non-toxic alkali or alkaline-earth metal salt without impairing the invention.

For preparing an immunogenic preparation adequate for administration to human beings, the freeze-dried complex is for instance dissolved in normal saline, gel-filtered e.g. on Sepharose 2B-CL (a product manufactured and sold by Pharmacia Fine Chemicals, Uppsala, Sweden) and the nonretarded fraction is dialysed against water, supplemented with a stabilizer, which is for instance a mono- or di-saccharide (e.g. lactose). The solution is then distributed into 5 ml glass vials in order to contain 5 $\mu$g (or a multiple thereof) of complex per dose and freeze-dried and the vials are tightly stoppered. Before administration by intramuscular or, preferably, subcutaneous route (preferably repeated once or twice) the vaccine is extemporaneously reconstituted by addition of pyrogen-free normal saline.

This invention also comprises a composition of matter useful for producing immunity against meningitis provoked by Haemophilus influenzae type b infection which comprises an immunogenic lipopolysaccharide-free capsular polysaccharide-protein noncovalent complex of Haemophilus influenzae type b wherein the polysaccharide moiety is polyribosylribitol phosphate (PRR'P) and wherein the protein moiety contains one methionine residue per molecule and shows by sodium dodecyl sulfate polyacrylamide gel electrophoresis (SDS-PAGE) two spots corresponding to ±90 and 10% (wt/wt) of polypeptides accounting for the protein present in the complex and corresponding to a main hydrophobic subunit having a molecular weight of about 40,000 and to a minor hydrophilic subunit having a molecular weight of about 27,000 respectively, the total amount of protein in the complex being in excess of 30% and preferably comprised between about 40 and 90% of the complex weight.

According to a preferred embodiment of the invention, the vaccine containing the PRR'P-protein complex is presented in freeze-dried form supplemented with a stabilizer (which is for instance a mono- or di-saccharide, e.g. lactose) and the vaccine is reconstituted by addition of pyrogen-free normal saline. The obtained pharmceutical composition is administered by subcutaneous or intramuscular route.

The PRR'P-protein complex of this invention is immunogenic not only in adults and children above 6 years of age but also in very young children i.e. children of less than 2 years of age, as indicated by clinical trials; it does not show any sign of toxicity in guinea pigs or mice, it is non pyrogenic when tested in rabbits at a dosage level of 0.125 $\mu$g per milliliter per kilogram of rabbit, showing also a negative limulus lysate gelation activity at 0.125 $\mu$g per milliliter.

The vaccine so prepared can be used in single or multiple injections to afford sufficient protection against infection caused by Haemophilus influenzae in humans, especially in children less than 2 year old. The single dosage level is from 5 $\mu$g to 100 $\mu$g, preferably also 2 or 3 such injections being given at two to twelve weeks intervals, e.g. eight weeks.

The invention is illustrated by the following examples which should not be construed as limiting the scope of the invention.

EXAMPLE 1

(a) Isolation of the PRR'P-protein complex

A pathogenic isolate of Haemophilus influenzae type b is grown in 20 l of liquid culture medium under conditions suitable for such growth to reach stationary phase, as described by P. Anderson et al. in Infect. and Immun. 13: 581–9: 1976.

The bacteria are then inactivated by addition of 20 g of cetrimonium bromide and the broth is centrifuged for 7 minutes at 7000 g. The pooled pellets are taken up in 300 ml of water and the suspension is centrifuged for 7 minutes at 7000 g. The sediment is taken up in 400 ml of 1.8 N calcium chloride in water and finely dispersed therein to yield a suspension which is vigorously shaken for one hour at 4° C. A 130 ml portion of ethanol 95% is then added and shaking is maintained for one other hour.

The suspension is centrifuged for 10 minutes at 20 000 g and the supernatant is diluted by addition of 1 860 ml of water.

The quaternary ammonium compound is precipitated by addition of 9.09 g of potassium iodide and the medium is stirred for one hour at 4° C. Centrimonium iodide is then discarded by centrifugation at 20 000 g at 4° C. and the supernatant is concentrated to 1/6.5 of its initial volume in a HOLLOW ultrafiltration apparatus (Amicon Corporation, Lexington, Mass., USA) equipped with a 50,000 daltons cut-off cartridge. The retentate is dialysed in a VISKING dialysis tubing (Serva Feinbiochemica, Heidelberg, Fed. Rep. of Germany), filtered through 3 successive membranes (0.8, 0.45 and 0.22 $\mu$m), distributed into glass vials and freeze-dried to yield crude PRR'P-protein complex.

(b) Purification of the PRR'P-protein complex and vaccine preparation

A 170 mg aliquot of crude complex is dissolved in 100 ml of 0.4 N sodium chloride in water and the solution is applied to a 2 l column of a Sepharose 2 B-Cl gel (Pharmacia, Uppsala, Sweden) equilibrated with 0.4 N sodium chloride in water. The non retarded fraction (90.22 mg of complex) is dialysed against water, supplemented with 3% (wt/vol) of lactose and the solution is sterilized by filtration through 0.45 and 0.22$\mu$ membranes and distributed into 5 ml glass vials containing each 5 $\mu$g (or a multiple thereof) of complex and freeze-dried. The vials are then tightly stoppered.

Before administration, the vaccine is reconstituted by addition of 0.5 to 5 milliliters of normal saline supplement with 0.25% phenol per vial.

(c) Physico-chemical characteristics of the purified complex

The protein moiety of the purified complex is mainly hydrophobic. Contrasting with the previously described complexes, SDS-PAGE analysis performed by adaptation of the method of Laemli (Nature 227: 680–685) using 3 mm thick gel, a concentration of 11% (wt/vol) of polyacrylamide gel and a tris/gylcerine buffer at pH 8.3 for the elution revealed the presence of only 2 polypeptides accounting for the composition of the protein: a main constituent (about 90% wt/wt) accounting for a 41,000 daltons fraction and a minor constituent (about 10% wt/wt) accounting for a 27,000 daltons fraction. The total protein content in the complex amounts of 54%.

Molecular weight distribution at different concentrations in SDS-PAGE indicated in Table I confirms remarkable homogeneity of the protein moiety.

TABLE I

| Amount deposited calculated in μg of protein | Molecular weight | |
|---|---|---|
| 50 | 41,000 | 27,000 |
| 25 | 41,000 | 27,000 |
| 12,5 | 41,000 | 27,000 |
| 6,25 | 41,000 | 27,000 |
| 3,125 | 41,000 | ND |
| 1,56 | 41,000 | ND |
| 0,78 | 41,000 | ND |
| 0,39 | ND | ND |

ND: not detectable.

The protein contains one methionine per molecule and its cleavage at the methionine site by the CNBr method yields two fragments of about 30,000 and 10,000 daltons respectively.

EXAMPLE 2

The technique is as described in Example 1, but the Eagan strain (P. Anderson et al. in J. Clin. Invest. 51, p. 31–38, 1972) is substituted for the wild isolate and there is obtained a purified complex showing a 62% (wt/wt) protein content, showing the same characteristics as those indicated for the complex obtained in Example 1.

EXAMPLE 3

The technique is as described in Example 1 wherein 0.4 N calcium chloride, 1 N calcium chloride, 1.8 N magnesium chloride, 0.2 N sodium chloride or 1.8 N sodium chloride is substituted for 1.8 N calcium chloride therein specified.

In these conditions, PRR'P-protein complexes with a protein content (wt/wt) of 34, 55, 58, 22 and 70% are obtained, respectively.

EXAMPLE 4

Preparation of polysaccharide-protein complex from capsulated Neisseria meningitidis group B A pathogenic isolate of *Neisseria meningitidis* group B is grown in liquid culture medium under conditions suitable for such growth to reach stationary phase, as described in U.S. Pat. No. 3,636,192.

A two liters aliquot of whole broth is inactivated by the addition of 0.1% (wt/vol) of cetrimonium bromide and the both is centrifuged for 7 minutes at 7000 g. After inactivation the pooled pellets are kept overnight at $-20°$ C. and then taken up in 40 ml of 1.8 N calcium-chloride at 4° C. and the resulting suspension is thoroughly homogenized and thereafter centrifuged for 7 minutes at 7000 g. The sediment is discarded and 25% vol/vol) of ethanol is added to the supernatant with vigorous stirring. Shaking is maintained for one hour at 4° C. after complete addition of the ethanol. The sediment is separated from the supernatant which is diluted up to a final concentration of 0.4 N in calcium chloride and cooled in an iced water bath.

Potassium iodide 1.5 M (3.66 ml) is then added and the medium is stirred for one hour at 4° C. and centrifuged at 20 000 g. The supernatant is concentrated up to a final volume of 50 ml in a Hollow ultrafiltration apparatus equipped with a 10,000 daltons cut-off cartridge and dialysed against water at 4° C.

The solution is filtered on a Sepharose 4 B Cl column and elution is performed with 0.4 N NaCl to yield a nonretarded fraction which is dialysed against water, supplemented with 5% (wt/vol) lactose, sterilized by filtration and freeze-dried to yield a complex with protein content of 60% (wt/wt).

EXAMPLE 5

Immunological properties of the PRR'P-protein complex

A. Immunogenicity of the PRR'P-protein complex in rabbits.

The immunogenicity of the PRR'P-protein complex has been assessed by administration to rabbits which, like human child under 2 years of age, are unable to elaborate an antibody response against the polysaccharide alone.

For this purpose, three successive doses of 10 μg PRR'P-protein complex per kilogram of body weight were injected intravenously to six rabbits on days 0, 4 and 8. The complex was obtained by using the technique described above; its protein content was 45% (wt/wt).

Booster doses were given on days 28, 32 and 36.

Each rabbit was periodically bled and the bactericidal and anti-PRR'P haemagglutinating antibody titres were determined in the sera preinactivated at 56° C. for 30 minutes.

The results are given in Table II, showing that a peak of antibody response (either bactericidal antibodies or anti-PRR'P antibodies) appears around day 15, the antibody titre dropping rapidly thereafter. Administration of a booster of the complex provokes a small and transient increase in the haemagglutinating antibody titre only.

TABLE II

| Immunogenicity of the PRR'P-protein complex in rabbits | | |
|---|---|---|
| Days after administration | Bactericidal antibodies (concentration expressed in $-\log_2$) | Anti-PRR'P haemagglutinating antibodies (concentration expressed in $-\log_2$) |
| →0 | 3 | 0 |
| →4 | 3.2 | 1.8 |
| →8 | 8.8 | 8.4 |
| 15 | 10.2 | 10.4 |
| 21 | 7.5 | 4.5 |
| →28 | 7.0 | 4.5 |
| →32 | 6.0 | 6.9 |
| →36 | 4.0 | 5.9 |
| 44 | 5.0 | 5.0 |
| 59 | 4.0 | 5.0 |
| 57 | 4.0 | 4.0 |

TABLE II-continued

Immunogenicity of the PRR'P-protein complex in rabbits

| Days after administration | Bactericidal antibodies (concentration expressed in $-\log_2$) | Anti-PRR'P haemagglutinating antibodies (concentration expressed in $-\log_2$) |
|---|---|---|
| 63 | 2.0 | 4.0 |
| 78 | — | 3.0 |

As control, the same dose of PRR'P alone (prepared by using the technique described by E. C. Gotschlich for groups A and C polysaccharides of *N. meningitidis* in U.S. Pat. No. 3,636,192) was administered to two rabbits, following the same schedule for administration, bleeding and antibody titre determination and no antibody response at all was detected.

In order to assess the relationship between protein content and immunogenicity of the complex, three doses of PRR'P-protein complex, each containing 2.5 μg of PRR'P per kilogramme of body weight were administered at 4 days intervals by intravenous route to five groups of 3 rabbits each, the percentage (wt/wt) of protein in the complex being 11, 30, 48, 69 and 86, respectively.

A sixth group of 3 rabbits was used as control following the same schedule but receiving same doses of PRR'P (2.5 μg) instead of PRR'P-complex.

All rabbits were bled at same time intervals and the anti-PRR'P antibody titres assessed by ELISA technique are given in Table III.

TABLE III

Relationship between immugenicity and protein content of the PRR'P-protein complex

| Days after first administration | PRR'P Antibody Titre (in Elisa units) Percent (wt/wt) of protein content of the complex | | | | | |
|---|---|---|---|---|---|---|
| | 0 | 11 | 30 | 48 | 69 | 86 |
| →0 | 0 | 0 | 0 | 0 | 0 | 0 |
| →4 | 2.7 | 2.8 | 3.0 | 1.6 | 1.2 | 3.6 |
| →8 | 10 | 19.2 | 19.2 | 36.7 | 25.7 | 13.0 |
| 12 | 15.8 | 20.0 | 28.2 | 117.5 | 96.7 | 87.5 |
| 15 | 16.7 | 37.5 | 26.7 | 141.7 | 130.0 | 145.0 |
| 19 | 25.8 | 21.7 | 27.5 | 69.2 | 68.3 | 112.0 |
| 22 | 25.8 | 31.7 | 39.2 | 59.2 | 53.3 | 42.5 |
| 25 | 63.3 | 36.7 | 31.7 | 53.3 | 48.3 | 55.0 |

From Table III, it appears that there is only a small increase in anti-PRR'P antibody titre after administration of either PRR'P alone or a PRR'P-protein complex containing 30% protein or less. Contrarily, complexes containing 48% protein or more are highly immunogenic, no substantial difference in immugenicity being observed with complexes having a protein content comprised between 48 and 85%.

In order to elucidate which class or classes of antibody are involved in the response to the complex, 5 rabbits were immunized with PRR'P-protein complex (obtained by using the technique of Example 1 and having a 45% (wt/wt) protein content) by intravenous administration of 3 successive doses of 10 μg per kilogramme of body weight on days 0, 4 and 8, followed by booster intravenous administration of same dose on days 43 and 46. The anti-PRR'P antibody titres were then assessed by haemagglutination at different times simultaneously in presence or in absence of 0.1 M 2-mercaptoethanol (i.e. a reagent being known to dissociate the IgM into their monomers, leaving the IgG intact). The results obtained for one rabbit are given in the following Table IV; the response pattern of the other rabbits gave comparable results differing mostly in the intensity of the response.

TABLE IV

Effect of 2-mercaptoethanol (2-ME) on the anti-PRR'P haemagglutinating antibody titre.

| Days after first administration | Anti-PRR'P haemagglutinating titre | |
|---|---|---|
| | without 2-ME | with 2-ME |
| →0 | 0 | 0 |
| →3 | 0 | 1 |
| →8 | 5 | 1 |
| 15 | 8 | 1 |
| 20 | 10 | 1 |
| →43 | 7 | 1 |
| →46 | 6 | 0 |
| 50 | >12 | 4 |
| 58 | 10 | 3 |
| 64 | 7 | 2 |
| 71 | 6 | 1 |

The figures of Table IV show that most of the haemagglutinating titre observed after the first 3 injections is due to IgM since most of the haemagglutination properties of the sera disappeared after mercaptoethanol treatment. Nevertheless, a slight residual haemagglutination indicates that small amounts of IgG are present from day 3 on.

After the last injections, a booster effect is observed either with or without the mercaptoethanol treatment, suggesting that both IgG and IgM are produced after the second series of injections. However, the IgG response is greater after the booster administration than after the initial injections.

Consequently the figures of Table IV demonstrate that both IgG and IgM are produced after immunization with the PRR'P-protein complex, suggesting that the PRR'P-protein complex is a thymodependent antigen.

Thymodependence is confirmed by the response pattern obtained when the PRR'P-protein complex is administered intravenously at day 0 and 2 weeks later.

The following Table V gives the anti-PRR'P antibody titres (expressed in Elisa units) obtained in rabbits injected intravenously on days 0 and 15 with 30 μg of a PRR'P-protein complex with a 45% (wt/wt) protein content.

TABLE V

Kinetics of the anti-PRR'P antibody response after immunization with the PRR'P-protein complex.

| Days after first administration | Anti-PRR'P antibody titres (ELISA units) | | |
|---|---|---|---|
| | rabbit 1 | rabbit 2 | rabbit 3 |
| 0 | 32 | 28 | 40 |
| 4 | 60 | 41 | 60 |
| 9 | 52 | 55 | 57 |
| 14 | 36 | 35 | 32 |
| → | | | |
| 16 | 48 | 36 | 43 |
| 18 | 112 | 74 | 104 |
| 22 | 161 | 149 | 35 |
| 28 | 40 | 46 | 34 |

B. Stimulation of rabbit spleen cells in-vitro (lymphoblastic transformation).

Three rabbits were immunized with either the PRR'P protein complex (45% (wt/wt) protein content) or the polysaccharide alone (3 successive injections of 10 μg of PRR'P-protein complex or PRR'P/kg body weight on day 0-4-8 according to the hereabove indicated schedule). The spleen of each rabbit was removed on day 15, which corresponds to the highest serum antibody titre of rabbits receiving the PRR'P-protein complex. The spleen cells were then cultivated for 5 days (at 37° C. in humidified atmosphere containing 5% $CO_2$ and at a cell density of $3.10^6$ cells/ml) using RPMI 1640 medium (as described by G. E. Moore et al. in J.A.M.A. 199: 519-524; 1967) and supplemented with L-glutamine, 2 mM; penicillin G, 100 IU/ml; 2-mercaptoethanol, $5.10^{-5}$ M and 10% normal rabbit serum in the presence of either the PRR'P-protein complex or the polysaccharide alone, at different concentrations from 1 to 100 μg/ml. At the end of the incubation period, $^3$H-thymidine (5 μCi) was added to the cultures and the cells were recovered and washed 18 hours later using an automatic harvester MASH II (Flow Laboratories Inc., Rockville, Md. USA).

The radioactivity incorporated in the cells was counted using a Packard Tri-Carb Liquid Scintillation Counter (Packard Instr. Co., Downers Grove, Ill., USA).

The results are presented in Table VI.

TABLE VI

In vitro stimulation of rabbit spleen lymphocytes by PRR'P and PRR'P-protein complex.

| Antigen conc. in the culture (μg/ml) | Counts per minute incorporated per culture ($\times 10^{-3}$) | | | |
|---|---|---|---|---|
| | Rabbits injected with PRR'P Stimulation by | | Rabbits injected with PRR'P-protein complex Stimulation by | |
| | PRR'P | complex | PRR'P | complex |
| 0 | 66 ± 34 | 66 ± 34 | 521 ± 221 | 512 ± 221 |
| 1 | 1157 ± 447 | 1025 ± 760 | 1419 ± 1392 | 5211 ± 1713 |
| 2.5 | 877 ± 293 | 2079 ± 1261 | 2985 ± 664 | 9276 ± 1056 |
| 5 | 830 ± 340 | 2202 ± 409 | 1916 ± 389 | 17116 ± 3232 |
| 10 | 862 ± 234 | 815 ± 318 | 3082 ± 344 | 25307 ± 5749 |
| 25 | 711 ± 360 | 624 ± 236 | — | 53369 ± 1108 |
| 50 | 717 ± 281 | 479 ± 147 | 3210 ± 580 | 77031 ± 3549 |
| 100 | 1481 ± 171 | 602 ± 306 | 651 ± 170 | 88544 ± 5463 |

Table VI shows that the spleen cells of rabbits immunized with PRR'P respond neither to the complex nor to the polysaccharide. This is in agreement with the absence of anti-PRR'P antibodies in the serum of rabbits immunized with the polysaccharide alone. On the other hand, spleen cells of rabbits immunized with the PRR'P-protein complex incorporate high levels of $^3$H-thymidine showing a high rate of proliferation in the presence of the PRR'P-protein, the proliferation being related to the antigen concentration. The spleen cells do not proliferate when the PRR'P alone is added instead of the PRR'P-protein complex.

From this experiment it can be concluded that, contrary to PRR'P alone, the PRR'P-protein complex is able to induce the proliferation of a population of T cells in the spleen of rabbits immunized with the PRR'P-protein complex. This population of T cells can be stimulated in vitro by the PRR'P-protein complex but not by PRR'P alone, suggesting that the determinant recognized by the T cells is present in the protein part of the complex.

The lymphoblastic transformation test was also used to detect the presence or memory cells in the spleen of rabbits a few months after immunization with PRR'P-protein complex.

For that purpose a rabbit was immunized with the PRR'P complex (45% (wt/wt) protein content) according to the hereabove indicated schedule (by three successive intravenous injections of 10 μg of PRR'P-protein complex per kg body weight with booster doses given at days 43-46). The booster administration induced a rapid increase in the anti-PRR'P antibody titre but, as expected, the titre dropped quickly during the next fifteen days.

Twenty days after the last booster dose administration, the antibody titre was less than one-fourth of the value reached on day 50.

The results are given in the following Table VII A.

TABLE VII A

Persistence of memory cells in the spleen: Kinetics of the antibody response.

| Day | Anti-PRR'P antibody titre (ELISA units) in the serum |
|---|---|
| →0 | 5.8 |
| →3 | 4.1 |
| →8 | 19.0 |
| 15 | 28.0 |
| 20 | 36.0 |
| →43 | 19.0 |
| →46 | 4.0 |
| 50 | 200.0 |
| 58 | 80.0 |
| 64 | 44.0 |
| 71 | 40.0 |

Further antibody titre decrease was shown experimentally 100 days after the initial immunization at the time of spleen removal.

The cells ($6.10^5$) isolated from the spleen were cultivated for 5 days at 37° C. in humidified atmosphere containing 5% $CO_2$ using RPMI 1640 medium supplemented with 10% autologous heat inactivated normal rabbit serum and containing different concentrations (up to 100 μg/ml) of either PRR'P or PRR'P-protein complex (45% (wt/wt) protein content). On the fifth day the cells were pulsed for 18 hrs with 1 μCi of 6 $^3$H-thymidine and the radioactivity incorporated in the cells was measured.

The results are given in Table VII B and show that the spleen cells proliferate in response to the PRR'P-protein complex but not to PRR'P alone.

It is concluded that memory cells (T cells) do persist in the spleen of rabbits immunized 3½ months previously and to which booster doses were given 1½ month after the initial immunization, at a time when no antibody is detected anymore in the serum.

TABLE VII B

Persistence of memory cells in the spleen: $^3$H-Thymidine uptake by spleen cells.

| Antigen concentration in the culture (μg/ml) | | Counts per minute incorporated by $6.10^5$ spleen cells ($\times 10^{-3}$) from rabbit injected with PRR'P-protein complex |
|---|---|---|
| 0 | | 792 |
| 1 | | 915 |
| 2.5 | | 976 |
| 5 | | 833 |
| 10 | PRR'P | 1380 |
| 25 | | 939 |
| 50 | | 831 |
| 100 | | 1113 |
| 0 | | 690 |
| 1 | | 858 |
| 2.5 | | 2432 |
| 5 | | 4592 |
| 10 | Complex | 6122 |

TABLE VII B-continued

Persistence of memory cells in the spleen:
$^3$H-Thymidine uptake by spleen cells.

| Antigen concentration in the culture (μg/ml) | Counts per minute incorporated by $6.10^5$ spleen cells ($\times 10^{-3}$) from rabbit injected with PRR'P-protein complex |
|---|---|
| 25 | 7957 |
| 50 | 7786 |
| 100 | 2422 |

The ability of the spleen cells removed at day 100 (as indicated hereinabove) to elaborate secondary antibody response in vitro has been assessed as follows:

The spleen cells were cultivated for 6 days at 37° C. in humidified atmosphere containing 5% $CO_2$ using round bottom plastic tubes at a concentration of $3.10^6$ cells/ml in one ml of RPMI 1640 medium supplemented with 2 mM glutamine, $5.10^{-5}$ M mercaptoethanol, 100 I.U./ml penicillin G, 100 μg/ml streptomycin and 10% heat inactivated normal rabbit serum. The antigen (PRR'P or complex) was added to the cultures at different concentrations up to 25 μg/ml.

After 6 days, the cells were washed by centrifugation with RPMI medium to remove the antigen and cultivated for one day using the same medium without antigen and one other day with the medium supplemented with 10% foetal calf serum to remove rabbit serum proteins. The cells were then washed and cultivated for 3 other days in the medium containing foetal calf serum. At the end of the culture period, the cells were sedimented and the supernatant was collected for anti-PRR'P antibody determination by ELISA technique, using a peroxydase-labelled goat anti-rabbit IgG.

The results are given in the following Table VII C; they clearly indicated that the spleen cells are able to produce anti-PRR'P antibodies in vitro when they are incubated with the PRR'P-protein complex; this response is dose-dependent and no production of anti-PRR'P antibodies is observed in response to the polysaccharide.

TABLE VII C

Persistence of memory cells in the spleen:
Anti-PRR'P antibodies production by spleen cells in vitro.

| Antigen concentration in the culture (μg/ml) | | Anti-PRR'P antibody titre (optical density at 450 nm) |
|---|---|---|
| 0 | | 0.141 |
| 1 | | 0.159 |
| 2.5 | | 0.161 |
| 5 | PRR'P | 0.168 |
| 10 | | 0.161 |
| 25 | | 0.169 |
| 0 | | 0.130 |
| 1 | | 0.353 |
| 2.5 | | 0.563 |
| 5 | complex | 0.575 |
| 10 | | 0.325 |
| 25 | | 0.310 |

EXAMPLE 6

I. Clinical trials in adolescents.

A group of 82 male and female healthy adolescents (15 to 16 year old) was divided into 2 subgroups of 41 each.

Prevaccinal sera were taken for antibody determination and PRR'P-protein vaccine obtained according to Example 1 was administered by subcutaneous route to the first subgroup, whereas a PRR'P vaccine was administered by the same route to the second subgroup.

The dosage which was 21 μg of PRR'P-protein complex for the first subgroup and 13.7 μg of PRR'P for the second subgroup with a booster administration in each subgroup, 4 weeks after the first injection.

The trials were performed under double blind conditions.

Among the subjects who where given the PRR'P-protein complex vaccine and after the first administration, 2 subjects reported a mild local erythema and one had a small headache and after the booster administration 2 reported mild general and local symptoms and one reported a local reaction.

Among the subjects who were given the PRR'P vaccine and after the first administration one subject showed a mild local and general reaction and after the booster administration, the same subject showed a mild local soreness.

The serological results obtained by ELISA showed a twofold or higher increase of seroconversion in 71% of the subjects who were given the PRR'P-protein complex vaccine and in 50% of the subjects who were given the PRR'P vaccine.

A twofold increase in bactericidal antibodies was observed in 75% and 63% of the subjects respectively.

II. Clinical trials in children.

A group of 71 male and female children (6 year old) was divided into 2 subgroups of 32 and 39 children respectively.

Prevaccinal sera were taken for antibody determination and PRR'P complex vaccine obtained according to Example 1 was administered by subcutaneous route to the first subgroup whereas a PRR'P vaccine was administered by the same route to the second subgroup.

The dosage unit was 10 μg of complex for the first subgroup and 6.35 μg of PRR'P for the second subgroup with a booster administration in each subgroup, 4 weeks after the first injection.

The trials were performed under double blind conditions.

Among the children who were given the PRR'P-complex vaccine and after the first administration 2 children reported a mild local erythema and after the booster administration, 2 children reported a mild soreness.

Among the children who were given the PRR'P vaccine and after the first administration, one child had a mild soreness, another one had headache and a third one had fever, and after the booster administration, 3 reported a mild local soreness.

The serological results obtained by ELISA showed a two fold or higher increase in anti-PRR'P antibody titre in 68.8% of the children after the first PRR'P-protein vaccine injection and 62.5% after the booster administration of the same vaccine and for the children who were given the PRR'P vaccine, the results were 71.8% and 76.9% respectively.

For bactericidal antibodies, the results were 66% and 75% for the first subgroup and 79% and 82% for the second subgroup, respectively.

III. Clinical trials in infants.

PRR'P-protein complex vaccine obtained according to Example 1 was administered by subcutaneous route to four infants (4–8 month old) following the hereinabove described vaccination schedule, the dosage unit being 13.5 μg per child.

Antibody titres (IgG, IgA and IgM) were assessed by ELISA before and after administration of the vaccine with a human standard containing 32 μg of Anti-PRR'P precipitating antibodies per milliliter. The results are summarized in Table VIII wherein the values between brackets give the fold increase after the first administration (Post-1) and after the booster administration (Post-2).

The figures show that, after the first administration, a two fold increase was obtained in 2 infants for IgG and in one infant for IgA or IgM. After the booster administration, a two fold increase was obtained in the 4 infants for IgG, in two infants for IgA and in one infant for IgM.

TABLE VIII

Anti-PRR'P antibody response after immunization of infants with the PRR'P-protein vaccine.

| | IgG (ng/ml) | | | | IgA (ng/ml) | | | | IgM (ng/ml) | | | |
|---|---|---|---|---|---|---|---|---|---|---|---|---|
| Infant N° | 1 | 3 | 4 | 5 | 1 | 3 | 4 | 5 | 1 | 3 | 4 | 5 |
| Age (mths) | 4 | 8 | 4 | 4.5 | 4 | 8 | 4 | 4.5 | 4 | 8 | 4 | 4.5 |
| Antibody titre | | | | | | | | | | | | |
| Pre vaccination | 160 | 520 | 360 | 240 | 0 | 880 | 320 | 480 | 350 | 1500 | 600 | 400 |
| Post - 1 | 400 | 880 | 560 | 640 | 440 | 960 | 400 | 560 | 1000 | 1400 | 850 | 700 |
| | (2.5) | (1.7) | (1.6) | (2.7) | (>44) | (1.1) | (1.3) | (1.2) | (2.9) | (0.9) | (1.4) | (1.8) |
| Post - 2 | 1320 | 1480 | 2560 | 520 | 400 | 480 | 5760 | 400 | 3400 | 2100 | 2950 | 1600 |
| | (8.3) | (2.8) | (7.1) | (2.2) | (>40) | (0.6) | (18.0) | (0.8) | (9.7) | (1.4) | (4.9) | (4.0) |

From the above results it appears that the PRR'P-protein complex of the invention and the PRR'P vaccine are equivalently valuable for immunizing adults and children without involving any substantial side effects. Moreover, the PRR'P-protein vaccine is also effective in young infants (below 18 months).

EXAMPLE 7

Antibody response of rabbits to Neisseria meningitidis group B polysaccharide-protein complex Protein-polysaccharide complex of *Neisseria meningitidis* group B as obtained in example 4 was injected intravenously to 3 rabbits on days 0, 4 and 8 at a dose of 10 μg of complex per kilogram of body weight. As a control, 3 rabbits of a second group were injected by the same route at 0, 4 and 8 days with *Neisseria meningitidis* group B polysaccharide (PSB) at a dose of 5 μg per kilogram of body weight. The rabbits of both groups were bled at 4 days intervals and the titre of anti-PS B antibodies was determined by ELISA in the successive sera. Bactericidal antibodies were assessed in the same sera by using either the strain from which the protein-polysaccharide complex was derived (strain containing the serotype antigen 2 or STA2) or by using a strain of group B but of a different serotype (containing the serotype antigen 6 or STA6). The last assay allows to discriminate between anti-PSB bactericidal antibodies and antibodies of different specificities. The results are summarized in Table IX. They clearly show that the complex but not the polysaccharide alone is capable of eliciting an anti-PSB antibody response. The antibody level is maximal between days 8 and 12 and decreases slowly afterwards to become not significant 30 days after the first administration. Bactericidal antibodies are also elicited by immunization with the complex. Some are bactericidal for the strain containing STA6 which has only PSB in common with strain STA2 and show the same kinetics as anti-PSB antibodies.

These results demonstrate that the anti-PSB antibodies induced by the complex in rabbits are bactericidal. The presence at day 30 of a significant concentration of antibodies bactericidal for the strain containing STA2 but not for the strain containing STA6 further indicates that some bactericidal antibodies are directed against the protein component of the complex.

In order to investigate whether the bactericidal antibodies present at day 30 were directed against the serotype antigen or to other somatic antigen, the serum of a rabbit immunized as above with a protein-polysaccharide complex obtained by the method of example 4, but containing 79% protein was used to test its content in bactericidal antibodies against several strains of *N. meningitidis* B containing different serotype antigens. The serum obtained 29 days after the first administration of the complex did not contain anti-PSB antibodies as shown by ELISA. This serum was bactericidal for the strain which was used to prepare the complex (containing STA2) and for several strains of *N. meningitidis* group B or group C but also containing STA2.

However, the serum was unable to kill bacteria having another serotype antigen (i.e. STA 1,4,6,8,9,11,12 and 14 respectively). Therefore it is concluded that the serotype antigen 2 (STA 2) is at least one of the components of the protein moiety of the complex described in example 4.

TABLE IX

Antibody response in rabbits immunized with the PSB-protein complex or the PSB alone.

| Days after first administration | ELISA anti-PSB antibodies* (optical density at 450 nm) | | Bactericidal antibodies* induced by complex (−log 2) strain containing | |
|---|---|---|---|---|
| | complex | PSB | STA2 | STA6 |
| →0 | 0.029 | 0.017 | 0 | 1.3 |
| →4 | 0.028 | 0.028 | 3.7 | — |
| →8 | 0.250 | 0.028 | 8 | 8 |
| 12 | 0.241 | 0.036 | 7 | — |
| 15 | 0.147 | 0.023 | 5.7 | 4 |
| 30 | 0.045 | 0.043 | 2.7 | 1.3 |

*Values are either the geometric mean (ELISA antibodies) or the arithmetic mean (bactericidal Ab) of the values obtained for the 3 rabbits.

We claim:

1. A process for preparing immunogenic lipopolysaccharide-free bacterial capsular polysaccharide-protein noncovalent complex from bacteria suspended in an aqueous medium which comprises inactivation of bacteria by the addition of a quaternary ammonium salt immediately followed by collection of the insoluble fraction, take-up with a 0.2 to 2 N aqueous solution of a non toxic alkali- or alkaline-earth metal salt, precipitation of contaminants by addition of 5 to 40% (vol/vol) of a water-miscible alcohol, removal of the quaternary ammonium salt from the solution by addition of a water soluble iodide, sulfocyanide or benzoate and separation of the precipitate to yield an aqueous solution from which the immunogenic lipopolysaccharide-protein noncovalent complex is isolated.

2. A process according to claim 1 wherein the bacteria is *Haemophilus influenzae* type b.

3. A process according to claim 1 wherein the bacteria is *Neisseria meningitidis* group B.

4. A process according to claim 1 wherein the aqueous medium is whole fermentation broth.

5. A process according to claim 1 wherein the quaternary ammonium salt is cetrimonium bromide.

6. A process according to claim 1 wherein the nontoxic metal salt is calcium chloride.

7. A process according to claim 1 wherein the amount of water-miscible alcohol is 25% (vol/vol) of ethanol.

8. A process according to claim 1 wherein the water soluble iodide is an alkali metal salt.

9. A process according to claim 1 wherein the isolation from the aqueous solution is performed by ultrafiltration and lyophilisation.

10. An immunogenic lipopolysaccharide-free capsular polysaccharide-protein noncovalent complex of Haemophilus influenzae type b prepared by the process of claim 1 wherein the polysaccharide moiety is polyribosylribitol phosphate and wherein the protein moiety presents one methionine residue per molecule and which, when tested by sodium dodecyl sulfate polyacrylamide gel electrophoresis, shows two spots corresponding to 90 and 10% (wt/wt) of polypeptides accounting for the protein present in the complex, the main fraction being hydrophobic and of a molecular weight of 41,000 daltons, the total amount of protein in the complex being at least 30% of the complex weight.

11. A complex according to claim 10 wherein the protein content is comprised between 40 and 90% (wt/wt) of the complex.

12. A meningitis vaccine comprising an effective dose of the polysaccharide-protein complex of claim 10 in freeze-dried form with a stabilizer.

13. A method for inducing active immunization against infection by *Haemophilus influenzae* type b in humans which comprises administering an effective amount of the polysaccharide-protein complex of any of claims 10 and 11.

* * * * *